Dec. 9, 1969 H. E. McCORMICK Plant Pat. 2,948
PERSEA GRATISSIMA (AVOCADO)
Filed Jan. 22, 1968
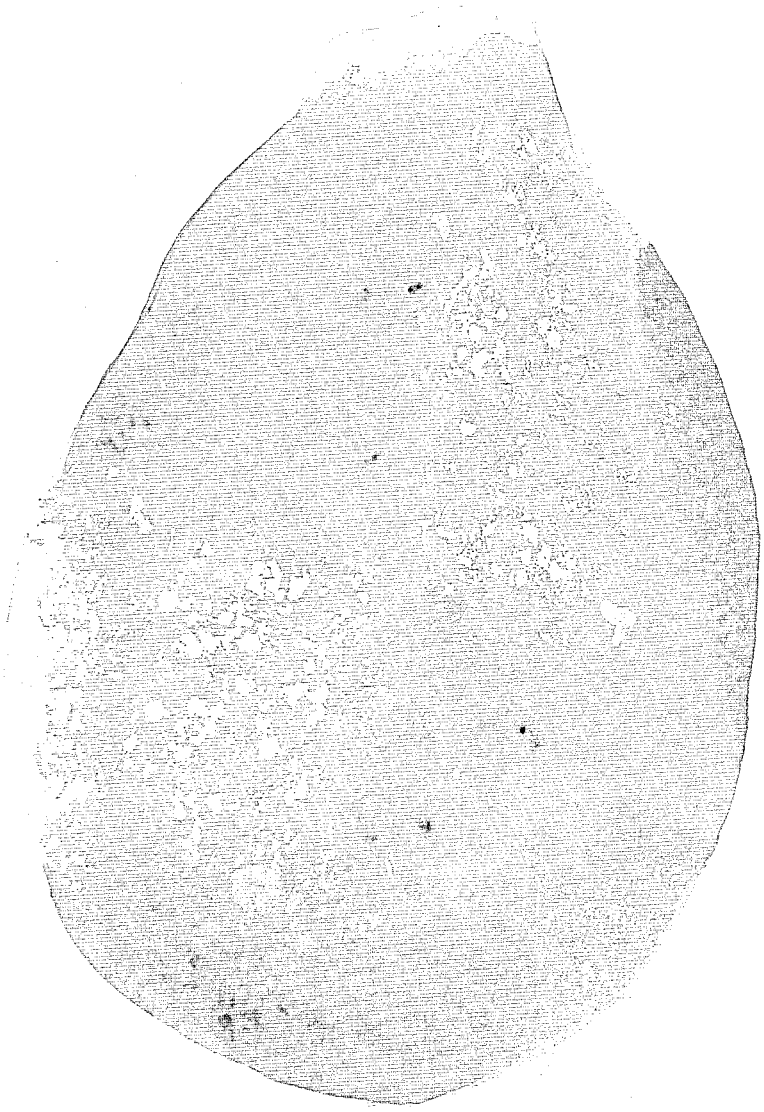
Howard E McCormick United States Patent Office Plant Pat. 2,948
Patented Dec. 9, 1969

2,948
*PERSEA GRATISSIMA* (AVOCADO)
Howard E. McCormick, 110 Atlanta Ave.,
Stuart, Fla. 33494
Filed Jan. 22, 1968, Ser. No. 703,223
Int. Cl. A01h *5/08*
U.S. Cl. Plt.—44 1 Claim Herewith description and other specifications of *Persea gratissima* (avocado) shown in application.

This fruit was discovered by applicant on the grounds of Mr. James W. Mills of 401 Alamanda Ave., Martin County, Stuart, Fla. This tree was one of several in the spacious yard of Mr. Mills. These trees are growing on sandy soil in a well protected area of Stuart and are well tended and all thrifty.

As a professional nurseyman of more than twenty years experience in this area I recognized the uniqueness and latent commercial possibilities of this fruit.

This fruit is a seedling avocado which was found growing among others and has a distinctively colored fruit of a rich red, flecked with yellow. The fruit is four to seven inches long, commonly pyriform, medium sized fruit 12 to 20 ounces, sometimes larger. Skin nearly smooth, flesh yellowish-green of pleasant, mild, nutlike, faintly sweet flavor. Seed medium tight in cavity. Season latter part of September through October. Tree rather upright in habit, moderately hardy to cold.

The outstanding characteristic of this fruit is the color. Authority for description of the colors describing this fruit may be found in the booklet "Enduring Colors for the Artist," a simplified technical treatise on permanance in paintings, published by Permanent Pigments, 2700 Highland Ave., Cincinnati, Ohio 45200. Also artist color chart published by same company.

The predominating color is Acra Crimson, with a background of Cadmium Yellow, light and flecked through some area of the red.

This fruit is presently being asexually reproduced by means of grafting, and the propagations exhibit the novel characteristics of the parent tree.

I claim:

1. A new and distinct variety of avocado as herein illustrated and described, being chiefly characterized by a fruit skin color of red flecked with yellow.

No references cited.

ROBERT BAGWILL, Primary Examiner